(12) United States Patent
Reis et al.

(10) Patent No.: US 8,337,468 B1
(45) Date of Patent: Dec. 25, 2012

(54) NEEDLESTICK INJURY PREVENTION DEVICE

(76) Inventors: Tonya Reis, LaPorte, TX (US); Cecilia Beeson, Deer Park, TX (US); Jamie Baggett, Houston, TX (US)

( * ) Notice: Subject to any disclaimer, the term of this patent is extended or adjusted under 35 U.S.C. 154(b) by 54 days.

(21) Appl. No.: 12/868,202

(22) Filed: Aug. 25, 2010

Related U.S. Application Data

(60) Provisional application No. 61/237,041, filed on Aug. 26, 2009.

(51) Int. Cl.
*A61M 5/32* (2006.01)
*A61M 5/00* (2006.01)
*A61M 5/315* (2006.01)

(52) U.S. Cl. ........ 604/198; 604/181; 604/187; 604/192; 604/218

(58) Field of Classification Search .................. 604/506, 604/192, 198, 240, 241, 242, 243, 181, 187, 604/218, 263
See application file for complete search history.

(56) References Cited

U.S. PATENT DOCUMENTS

| | | | |
|---|---|---|---|
| 4,820,275 A * | 4/1989 | Haber et al. ................ | 604/198 |
| 6,171,284 B1 | 1/2001 | Kao et al. | |
| 6,783,002 B1 | 8/2004 | Pavlo | |
| 6,846,302 B2 | 1/2005 | Shemesh et al. | |
| 7,159,713 B1 | 1/2007 | Austria | |
| 7,226,431 B1 | 6/2007 | Bell-Greenstreet | |
| 7,300,421 B1 | 11/2007 | Lowry et al. | |
| 7,513,888 B2 | 4/2009 | Sircom et al. | |
| 2009/0157088 A1* | 6/2009 | Mengato ..................... | 606/102 |

\* cited by examiner

*Primary Examiner* — Kevin C Sirmons
*Assistant Examiner* — Shefali Patel
(74) *Attorney, Agent, or Firm* — Andrew W. Chu; Craft Chu PLLC

(57) ABSTRACT

The present invention is a device for protecting against needlestick injuries, including a syringe, a sheath, an actuator, and a button. The syringe has a tube, plunger, and a needle in a hub. The sheath covers the needle in a first position, and the needle protrudes from a hole in the sheath in a second position. The plunger can be pressed to dispense from the tube in the second position. The actuator controls the movement between positions, and the button is the manual control for activating the actuator. The syringe extends through the sheath and actuator, such that the sheath and actuator can be adjusted for any type of syringe. A single hand can operate the button and the plunger.

8 Claims, 4 Drawing Sheets

NEEDLESTICK INJURY PREVENTION DEVICE

RELATED U.S. APPLICATIONS

The present application claims priority under U.S. Code Section 119(e) from a provisional patent application, U.S. Patent Application No. 61/237,041, filed on 26 Aug. 2009 and entitled "STIK-STOP".

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to a safety device to reduce occupational hazards in the medical field. More particularly, the present invention relates to a device to prevent needlestick injuries, especially during surgical procedures. Even more particularly, the present invention relates to a sheath for a needle.

2. Description of Related Art Including Information Disclosed Under 37 CFR 1.97 and 37 CFR 1.98.

A needlestick injury or "needlestick" is a piercing wound from a needle point or other sharp instrument. These injuries are commonly experienced by people handling needles in the medical field. When drawing blood, administering an intramuscular or intravenous drug, or performing other procedures involving sharps, the healthcare worker can be injured with the needle slips. Generally, needlesticks cause only minor bleeding or visible trauma. Scalpel injuries tend to be larger than a needlestick. Needlestick injuries are not limited to the medical community. Any environment where sharps are encountered poses a risk, such as police work.

A needlestick injury is an occupational hazard, especially in the operating room during surgery. These injuries are important to avoid because of the risk of transmitting blood-borne diseases, such as the hepatitis B virus (HBV), the hepatitis C virus (HCV), and the Human Immunodeficiency Virus (HIV), the virus which causes AIDS. Several agencies regulate the standards and controls to reduce these occupational hazards.

There are particular concerns for needlesticks, when using the current safety devices. For example, there are already known caps and sheaths to protect healthcare workers. However, needlesticks continue to occur as a result of not recapping the needle or misjudging alignment of the needle and cap during recapping. Especially during surgery and in the operating room, surgical needles may be left uncapped and exposed for repetitive use in a procedure, increasing the risk of inadvertently penetrating the glove and skin of the surgeon or assistant.

Various patents have issued in the past relating to preventing needlestick injuries. For example, U.S. Pat. No. 6,171,284, issued to Kao, et al. on Jan. 9, 2001, describes a syringe needle cover structure comprised of a sleeve, a coil spring, and a mount. The sleeve is installed over the syringe needle, and a press release section is situated along the two exterior sides. The coil spring is installed into the center section of the sleeve, and the mount is then attached to the lower section of the said sleeve. The structure is installed over a syringe needle, wherein the user only has to pull down the protective head without removing the syringe needle cover to utilize the syringe. After use, the mount is rotated counter-clockwise to re-cover the syringe needle.

U.S. Pat. No. 7,226,431, issued to Bell-Greenstreet on Jun. 5, 2007, discloses single-use enhancements to disposable syringes. The syringe has a stem and plunger with a disk called a "spider" held near the lower end of the stem. The plunger furthermore comprises a stem extension in the shape of a short cylinder, affixed to the lower face of the spider. Finally the plunger comprises a handle affixed to the upper end of the stem. In addition, the syringe comprises a lower seal and upper seal both of cylindrical annular shape made of rubbery material. In operation, the lower seal, the plunger and the upper seal are located at the bottom of the barrel. As the syringe reaches its final state, it becomes unusable for any subsequent use because the lower seal cannot be drawn upward and the upper seal is abandoned and remains at the top of the barrel.

U.S. Pat. No. 6,783,002, issued to Pavlo on Aug. 31, 2004, teaches another anti-needlestick system. The needle has flexible wings, and a shield assembly is formed as a generally planar sheet with long side edges and short end edges and a slot for receiving the wings, when held together and adapted to be placed beneath the wings above a patient's skin. There is a male section of the shield assembly on one side of the slot, and there is a female section on the other side of the slot. Each section has an upwardly facing side wall along the side and end edges of the planar sheet. A locking member formed in the side wall includes a male locking member and a co acting female receptacle.

U.S. Pat. No. 7,513,888, issued to Sircom, et al. on Apr. 7, 2009, discloses more needle guards. Each needle guard includes a canting plate locked on the needle shaft, during retraction of the needle tip within the guard and extension of the needle tip from the guard. The plate rotates into locking engagement with the shaft of the needle, when withdrawing the need from the guard. The plate protects healthcare workers from needlesticks.

U.S. Pat. No. 7,300,421, issued to Lowry, et al. on Nov. 27, 2007, describes another safety syringe with an adapter. The invention includes adapter for a standard syringe, vacuum tube or other medical device, so that the syringe can engage a protective sheath. The sheath can be deployed automatically upon activation of a release member with a single hand in order to propel the protective sheath from a retracted position to an extended position covering a needle. An elastic member can also propel the protective sheath from a retracted to an extended position.

U.S. Pat. No. 7,159,713, issued to Austria on Jan. 9, 2007, describes a sharp blade protection device, which is related to blades and other sharps. The user inserts and removes the sharp from the device so that training of use is minimized if needed at all. The device is usable with a single hand. There is a retention post for the sharp. This device is designed to be reusable and cleanable but is capable of inexpensive manufacturing as a disposable device.

U.S. Pat. No. 6,846,302, issued to Shemesh, et al. on Jan. 25, 2005, discloses another needle protector device, comprising a protector tube slidingly disposed in an outer tube and slidingly disposed over a syringe comprising a needle. The protector tube has at least one abutment initially in engagement with the outer tube such that the protector tube is constrained from moving distally with respect to the syringe. A guide inside the outer tube provides an urging force on the protector tube in a direction that tends to urge the protector tube distally towards a tip of the needle. A release mechanism moves the abutment out of engagement with the outer tube upon distal pushing of a plunger of the syringe, such that when the at least one abutment is out of engagement with the outer tube, the guide directs the protector tube distally towards the tip of the needle.

It is an object of the present invention to provide a device to protect against needlestick injuries.

It is another object of the present invention to provide a protection device, which sheaths the needle.

It is a further object of the present invention to provide a protection device which retracts the needle.

It is another object of the present invention to provide a protection device for operation by a single hand.

It is still another object of the present invention to provide a protection device with single use and disposable options.

It is another object of the present invention to provide a device to allow reuse of solutions, anesthetics, and other chemicals.

It is another object of the present invention to provide a protection device compatible with existing syringe and needle products.

It is yet another object of the present invention to provide an easy and effective way to prevent being stuck by uncovered needles.

These and other objects and advantages of the present invention will become apparent from a reading of the attached specification and appended claims.

SUMMARY OF THE INVENTION

The present invention is a device for protecting against needlestick injuries. The device includes a syringe, a sheath, an actuator, and a button. The syringe has a tube, plunger, and a needle in a hub. The fluid for delivery is loaded into the tube. The sheath covers the needle in a first position, so that needlestick injuries are prevented. The needle protrudes from a hole in the sheath in a second position, so that the syringe can deliver the fluid to the patient. The plunger can be pressed to dispense from the tube in the second position. The actuator controls the movement between positions, such that the syringe moves within the device. The button is the manual control for activating the actuator between positions. The sheath is held in place by the hand of the user, while the thumb of the same hand engages the button. The syringe extends through the sheath and actuator, such that the sheath and actuator can be adjusted for any type of syringe. A single hand can operate the button and the plunger.

The actuator means and buttons means include various structures to control the movement of the syringe within the device. The button can be a pushbutton, a lever switch, a rod, or a rotary member. The actuator includes springs and cams to attach to the syringe and move the syringe relative to the sheath. Controlled movement by click activation of the actuator allows for safety and convenient storage and use of the syringe.

DETAILED DESCRIPTION OF THE DRAWINGS

Figure 1:
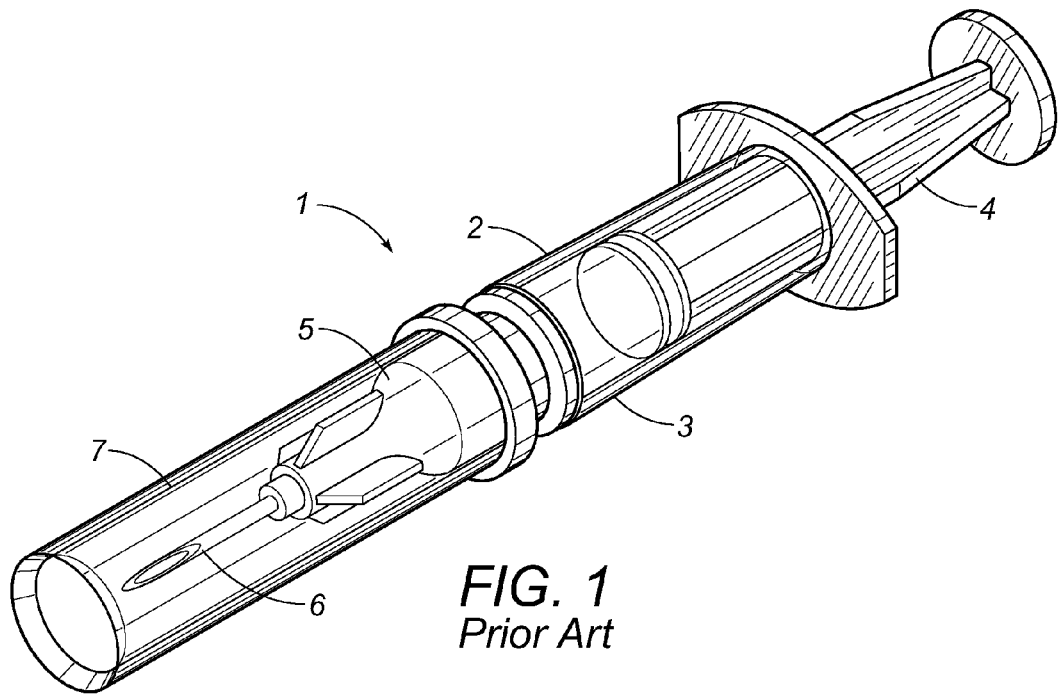
FIG. 1 is a perspective view of the prior art syringe with a manually placed cap.

The conventional device for protecting against needlestick injuries is shown in FIG. 1. This prior art device 1 includes a syringe 2 with basic structures. The tube 3 holds the fluid to be delivered to the patient. The plunger 4 creates a seal with the interior of the tube 3, such that movement of the plunger 4 either draws fluid into the tube 3 or dispenses fluid from the tube 3. At the end opposite the plunger 4, there is a hub 5, and a needle 6 is mounted on the hub 5. The hub 5 engages the tube 3 to create a pressure seal, such that fluid flows out of the hollow needle 6 from the tube 3. FIG. 1 shows a prior art cap 7, which covers the needle 6. In this device 1, the syringe 2 covered, preventing needlesticks. The prior art includes other manually operated caps, which require use of both hands in order to cover the needle.

Figure 2:
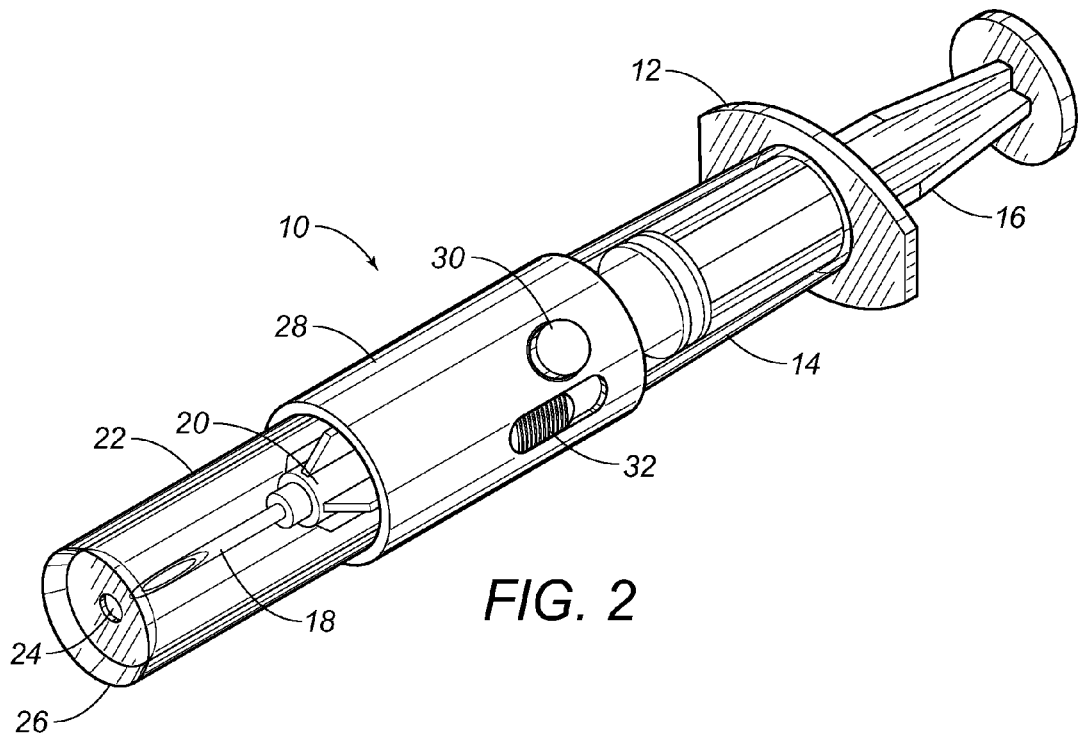
FIG. 2 is a perspective view of the protection device of the present invention in the first position with the needle within the sheath for safety.
Figure 3:
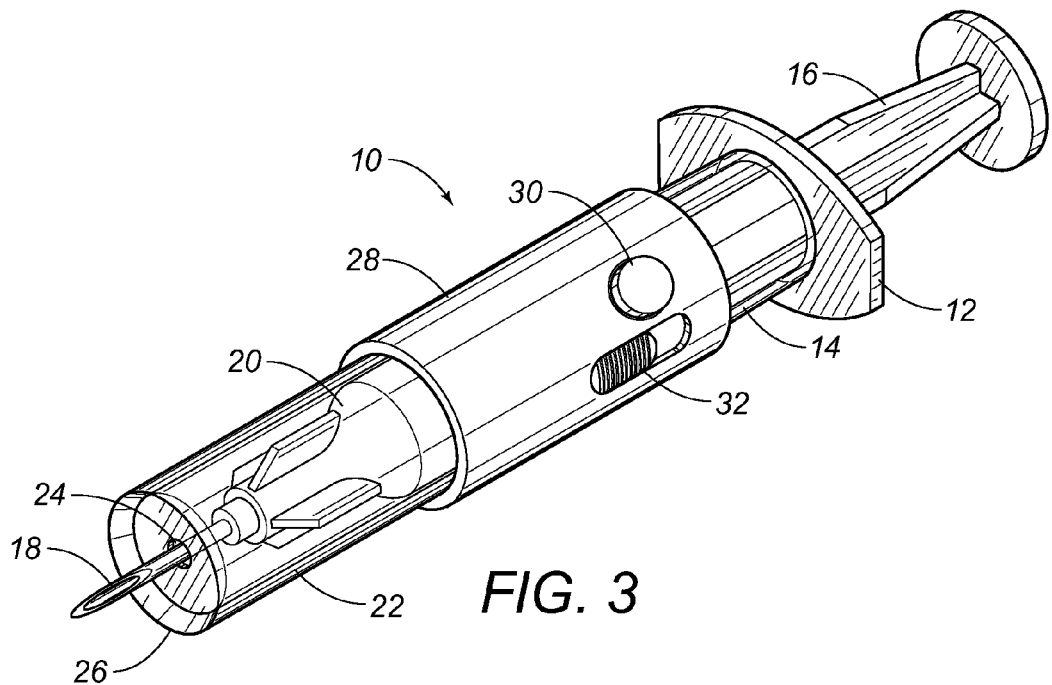
FIG. 3 is another perspective view of the protection device of the present invention in the second position with the needle protruding from the sheath for use in delivery of the contents of the tube.

The present invention improves upon this prior art technology in the form of a protection device 10, shown in FIGS. 2 and 3. The present invention includes a syringe 12, which is also comprised of a basic structures: a tube 14, a plunger 16 within the tube 14 in liquid-tight connection, and a needle 18 mounted in a hub 20. The hub 20 is placed at a tip of the tube 14 on an end opposite the plunger 16. These basic structures make the present invention compatible with all types and sizes of existing syringes. The syringe 12 is operated by moving the plunger 16 back and forth, within the tube 14. This basic action is not hindered by the present invention.

FIGS. 2 and 3 also show a sheath means 22 for covering the needle 18, wherein FIG. 2 shows the needle 18 in the sheath means 22 and FIG. 3 shows the needle 18 protruding from the sheath means 22. The sheath means 22 functions as a protective shield against needlestick injuries in the position shown in FIG. 2. The tip of the needle 18 cannot contact any patient or healthcare worker when in place around the needle 18. The sheath means 22 has a hole 24 at a distal end 26 thereof, such that a first position is set when the needle 18 is housed in the sheath means 22 (FIG. 2) and a second position is set when the needle 18 protrudes from the sheath means 22 (FIG. 3). The sheath means 22 is hollow with the syringe 12 being completely removably engaged to the sheath means 22. Additionally, the sheath means 22 is generally cylindrical in FIGS. 2 and 3. The sheath means 22 of the present invention may also have various different shapes, compatible with a syringe or even a non-cylindrical syringe.

The present invention 10 also includes an actuation means 28 for moving between the first and second positions. Importantly, the actuation means 28 is placed in closer proximity to the plunger 16 than to the hub 20. This position allows for use of the device 10 with only a single hand. The sheath means 22 can be gripped by the fingers of the user, and the thumb engages the actuation means 28. Furthermore, the thumb may also be able to engage the plunger 16 for accomplishing the sheathing and fluid delivery in one hand. The actuation means 28 is also hollow, such that the syringe 12 passes through the actuation means 28. The device 10 can be sized to fit a variety of different syringe 12 sizes. It is important to note that the syringe 12 is fixably attached to and within the actuation means 28. The fixed connection between the syringe 12 and actuation means 28 links the movement of the syringe 12 relative to the sheath means 22 with the actuation means 28. The syringe 12 extends through the actuation means 28 and the sheath means 22, and the plunger 16 remains actuatable for dispensing from the tube 14. The needle 18 is in either first or second position relative to the sheath means 22.

Figure 4:
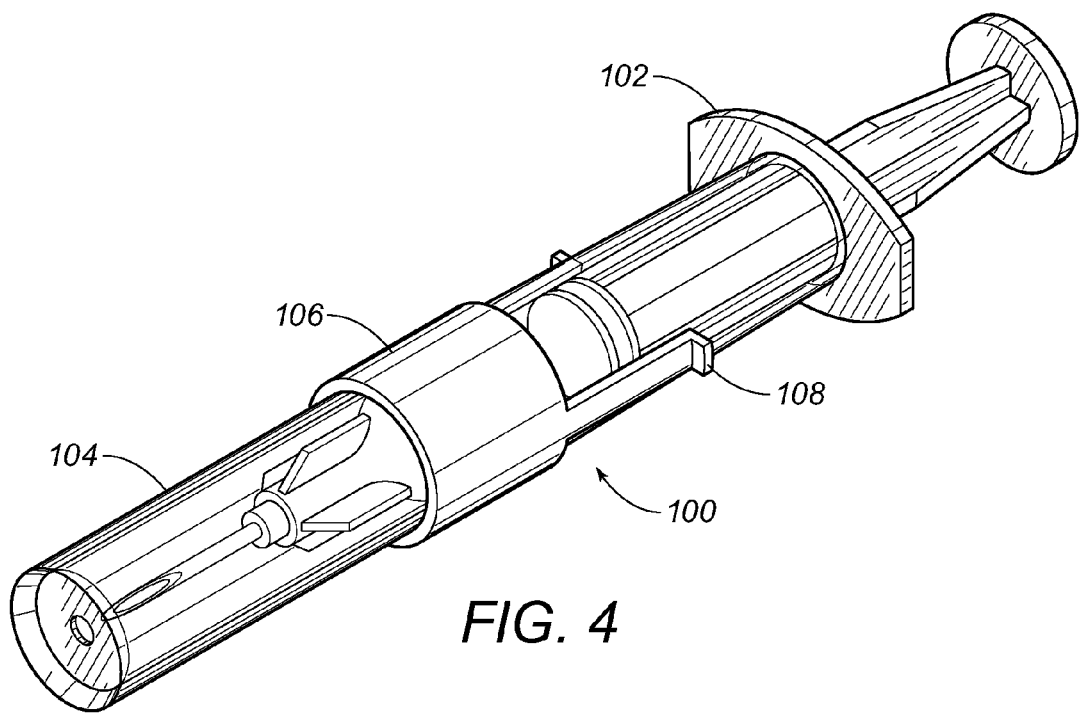
FIGS. 4, 5 and 6 are also schematic views showing the protection device of the present invention with alternate embodiments of the actuator.
Figure 5:
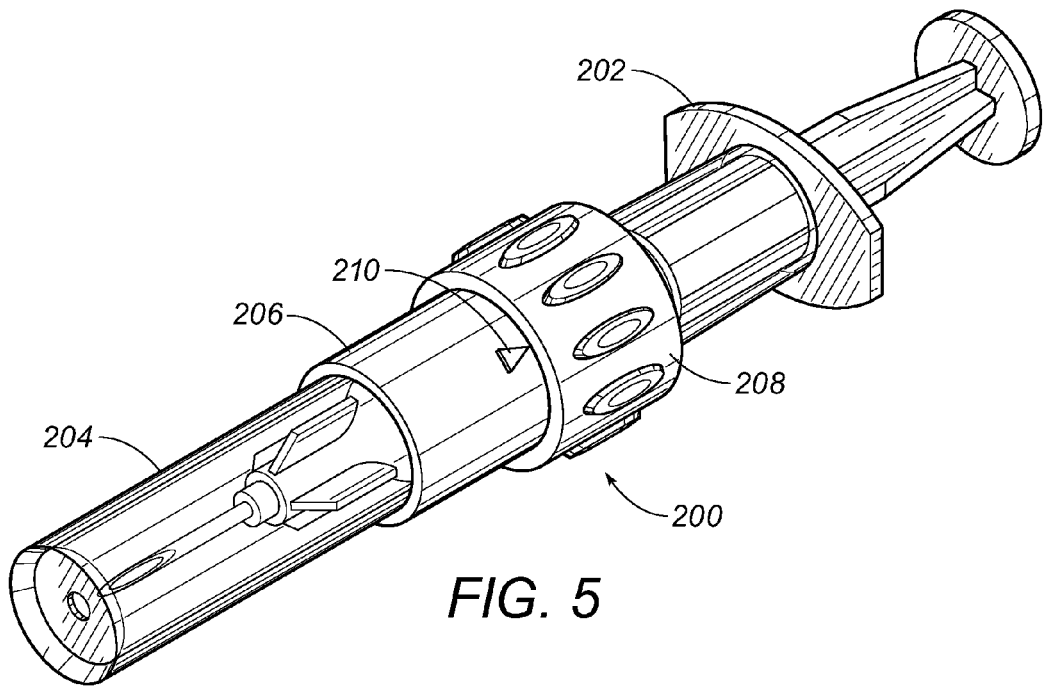
Figure 6:
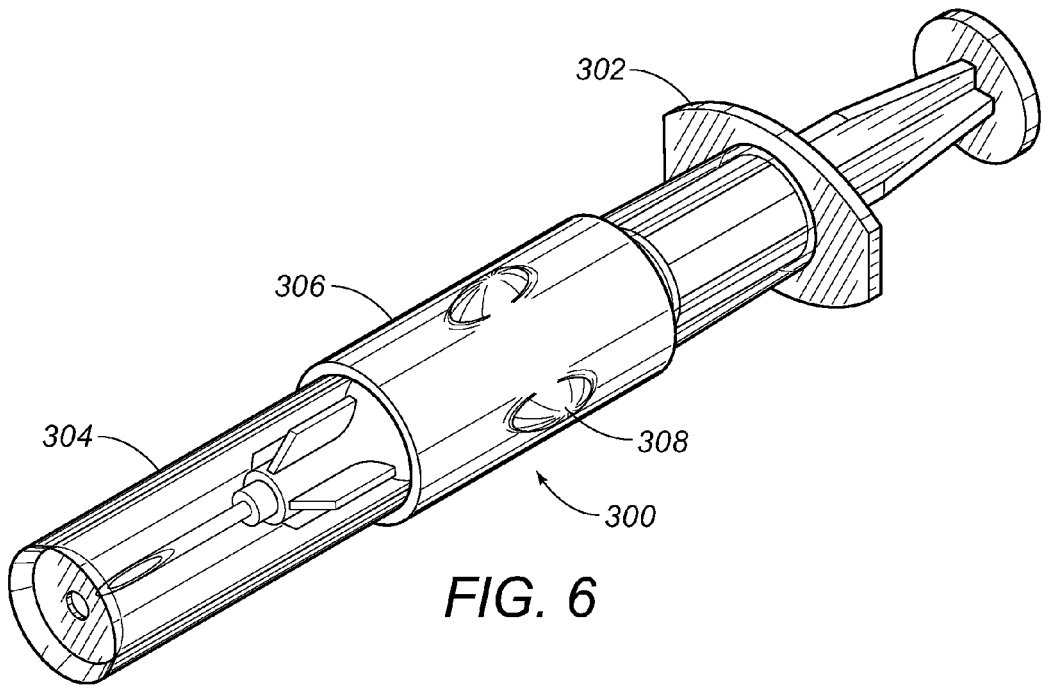

FIGS. 2 and 3 also show a button means 30 for manual control of the actuation means 28. The button means 30 is placed closer to the end of the tube 14 with the plunger 16 in order to facilitate the single hand action of the device 10. A pressbutton 30 is shown in FIGS. 2 and 3, and other button means 30 are also known. FIGS. 4, 5, and 6 all show various embodiments of the button means 30. FIG. 4 shows a device 100 with the syringe 102, sheath means 104, and actuation means 106. The button means 108 is a push rod, which can be activated by pressing the rod toward the needle end. Another possibility is shown in FIG. 5, wherein the button means 208 of the device 200 is a rotary device. Using a single hand, the thumb of the user can spin the button means 208 to force the actuation movement of the actuation means 206. The syringe 202 and sheath means 204 are moved in the same manner as the previous embodiment for the protective function. FIG. 6 shows yet another variation of the device 300 of the present invention with a button means 308. In this example, the button means 308 is a raised bump on the actuation means 306. Squeezing the bump activates the actuation means 306 to move the syringe 302 relative to the sheath means 304. Additional button means are possible for the present invention, including switches or levers. Importantly, the button means 30 must be compatible with single hand use and placement in relative close proximity to the plunger 16.

FIGS. 2 and 3 also show a locking means 32. This locking means 32 can prevent inadvertent activation of the button means 30. FIGS. 2 and 3 show the locking means 32 as a slide member that blocks the pressbutton of the button means 30 from being pressed. Other known locking means 32 may also be part of the present invention 10. This locking means 32 must also be placed in closer proximity to the plunger 16 and the actuation means 28 than to the hub 20. A single hand is able to engage the locking means 32, the button means 30, and the plunger 16. Another variation is shown in FIG. 4 with the rotary button means 208 on the device 200. There is a status indicator 210 on the actuation means 206, which provides a visual cue to identify the locked or unlocked or sheathed or unsheathed status of the device 200. Other status indicators 210 can be used for the other various embodiments of the device in any of the FIGS. 2-5.

Figure 7:
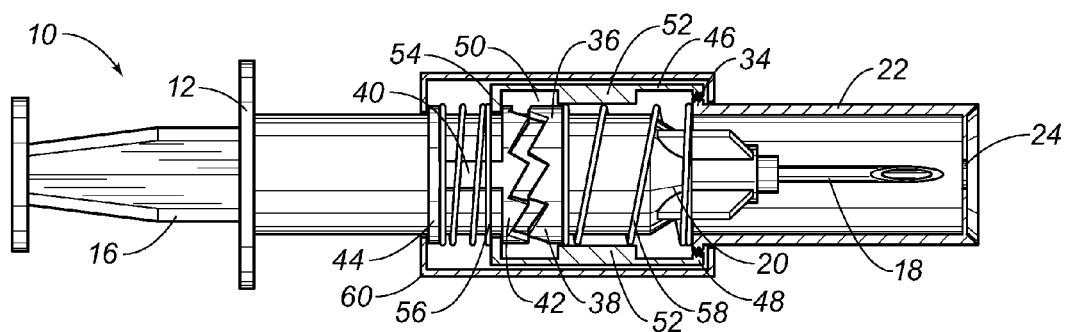
FIGS. 7 and 8 are partial sectional and schematic views of another embodiment of the protection device of the present invention, FIG. 7 showing the first position for safety and FIG. 8 showing the second position for delivery from the syringe.
Figure 8:
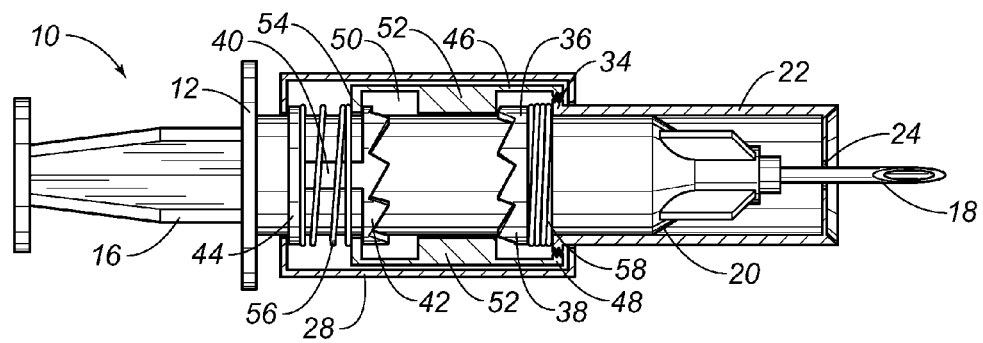

FIGS. 7 and 8 show partial sectional and schematic views of a more particular embodiment of the sheath means 22 and actuation means 28 of the device 10 of the present invention. This embodiment is illustrative of a single embodiment only. Similar to FIGS. 2 and 3, FIGS. 7 and 8 show a sheath means 22 for covering the needle 18, wherein FIG. 7 shows the needle 18 in the sheath means 22 and FIG. 8 shows the needle 18 protruding from the sheath means 22. FIGS. 7 and 8 show the attachment of the syringe 12 to the sheath means 22 and the actuation means 28. The sheath means 22 has screw threads 34 at an end opposite the hole 24.

The actuation means 28 includes a toothed sleeve 36 fixedly attached and friction fit to around the syringe 12, having teeth 38 pointed away from the needle 18. This toothed sleeve 36 is fixed connection to any size syringe 12. In particular, the toothed sleeve 36 may attach to the tube of the syringe 12. Movement is translated to the syringe 12 through this connection. The actuation means 28 further includes a sleeve cam 40 with complementary teeth 42 to engage the toothed sleeve 36 and an abutment member 44. The actuation means 28 has a collar member 46 with complementary screw threads 48, which engaging the screw threads 34 of the sheath means 22. The screw threads 48 connect the sheath member 22 to the actuation means 28, even though the sheath means 22 slides into the actuation means 28. The collar member 46 has an interior volume 50 housing the toothed sleeve 36 and the sleeve cam 40, and there are protrusions 52 within the volume 50 extending inward to engage the teeth 38 of the toothed sleeve 36. The collar member 46 further includes a complementary abutment member 54 at an end opposite the screw threads 48.

There are springs to power the single hand "click" action of the actuation means 28. A first compression spring 56 extends between the abutment member 44 of the sleeve cam 40 and the complementary abutment member 54 of the collar member 46. A second compression spring 58 extends between the toothed sleeve 36 and the sheath means 22. A shell member 60 covers the collar member 46 and connection between the sheath means 22 and the actuation means 28.

The button means 30 moves the sleeve cam 40 relative to the collar member 46. For example, the shell member 60 can abut against the complementary abutment member 44 of the sleeve cam 40 on a side opposite the first compression spring 56. The button means 30 in this instance moves the shell member 60 to move the sleeve cam 40, compressing the spring 56. Alternate button means 30 move the sleeve cam 40 with or without using the shell member 60. FIGS. 2, 3, and 5 are possible examples of a button means 30 moving the sleeve cam 40 without affecting the shell member 60.

The device 10 of the present invention uses "click" action to move the needle 18 between the first position (sheathed) and the second position (unsheathed). The button means 30 engages the sleeve cam 40 to compress the first compression spring 36 by the abutment member 44 towards the complementary abutment member 54 of the collar member 46. The sleeve cam 40 pushes the toothed sleeve 36 toward the screw threads 34, and the sleeve cam 40 stops when the teeth 38 of the toothed sleeve 36 engage the protrusions 52 of the collar member 46 and release the complementary teeth 42. Then, the first compression spring 56 returns to full extension, and the second compression spring 58 is compressed. The needle 18 is now in the second position. The teeth 38, complementary teeth 42, and the protrusions 52 are shaped in slanted or sloped forms to be coordinated. A gradual abutment is formed, such that the click action is the transition from mounting and releasing the teeth 38 on the protrusions 52.

To release the teeth 38, the button means 30 engages the sleeve cam 40 to compress the first compression spring 56 by the abutment member 44 towards the complementary abutment member 54 of the collar member 46 again. This time, the complementary teeth 42 of the sleeve cam 40 engage the teeth 38 of the toothed sleeve 36 until the teeth 38 disengage from or slide off the protrusions 52. The first compression spring 56 returns to full extension, and the second compression spring 58 returns to full extension. The needle is now in the first position. The needle 18 is returned to the sheath means 22, as the amount of compression of the second compression spring 58 set the amount of displacement of the needle 18 relative to the sheath means 22.

The present invention further includes a third position, corresponding to retracting the needle 18 even further. The toothed sleeve is shaped with teeth and protrusion for these multiple levels of displacement of the second compression spring. Furthermore, the actuation means and sheath means correspond in shape to the syringe for fixed engagement of the toothed sleeve. Even if the syringe is not cylindrical, the actuation means and sheath means can be adapted. The present invention includes non-cylindrical structures. The sheath means can be linear along a side of the syringe, and the corresponding structures adapt according to this placement. The actuation means can also be made linear or rectangular or another shape compatible with the syringe.

The method of protecting against needlestick injuries, using the device of the present invention includes covering a needle of a syringe with a sheath, attaching an actuator fixedly to the syringe, moving the needle to the second position for transferring to and from the tube, moving the needle to the first position for storing the syringe for repeat access, repeating movement from the first position and the second position until completing use of the syringe, and disposing of the syringe after use. The syringe is comprised of a tube, a plunger within the tube in liquid-tight connection, and the needle mounted in a hub. The sheath has a hole at a distal end thereof. The needle is housed in the sheath in a first position relative to the sheath. The actuator moves the needle from the first position to a second position and between the first and second positions. The needle being protruded from the sheath through the hole in the second position. The method may include engaging a lock when the needle is in the first position, and releasing the lock to move the needle from the first position to the second position.

The present invention provides a device to protect against needlestick injuries. The needle is sheathed or even retracted to increase safety for those handling the syringe. The syringe can be fitted with the other parts of the device before any contact so as to reduce risk of injuries while setting up the device. The protection device of the present invention operates by a single hand, which is important for surgical situations. The syringe is used more than once, and the syringe is left laying on a tray or cart near healthcare workers. The present invention has particular applicability to operating room procedures, where it is common to require syringes to be close by and immediately ready for use. The present invention also presents single use and disposable options, depending upon the materials used to construct the parts. The sheath and actuator can even be adjusted to be compatible with existing sizes and types of syringes and other sharps. Proper precautions, such as the sheath in the present invention, can be invaluable for avoiding needlesticks in other situations besides the operating room. Additionally, the device allows reuse of solutions, anesthetics, and other chemicals. The present invention is an easy and effective way to prevent being stuck by uncovered needles.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

We claim:

1. A device for protecting against needlestick injuries, comprising:
    a syringe, being comprised of a tube, a plunger within said tube in liquid-tight connection, and a needle mounted in a hub, said hub being placed at a tip of said tube on an end opposite said plunger;
    a sheath means, covering said needle and having a hole at a distal end thereof, said needle being housed in said sheath means in a first position and being protruded through said hole in a second position, said sheath means being hollow with said syringe being removably engaged to said sheath means;
    an actuation means for moving said needle between the first and second positions, said actuation means being placed in closer proximity to said plunger than to said hub, said actuation means being hollow with said syringe being fixably attached to said actuation means; and
    a button means for manual control of said actuation means,
    wherein said syringe extends through said actuation means and said sheath means, and wherein said plunger is actuatable for dispensing from said tube when said needle is in either the first or the second position relative to said sheath means,
    wherein said sheath means has screw threads at an end opposite said hole,
    wherein said actuation means comprises:
        a toothed sleeve fixedly attached and friction fit to around said syringe, having teeth pointed away from said needle;
        a sleeve cam with complementary teeth to engage said toothed sleeve and an abutment member;
        a collar member with complementary screw threads, engaging said screw threads of said sheath means, said collar member having an interior volume housing said toothed sleeve and said sleeve cam and protrusions extending inward to engage said teeth of said toothed sleeve and a complementary abutment member at an end opposite said screw threads;
        a first compression spring extended between said abutment member of said sleeve cam and said complementary abutment member of said collar member;
        a second compression spring extended between the toothed sleeve and said sheath means; and
        a shell member covering said collar member, and
    wherein said button means moves said sleeve cam relative to said collar member.

2. The device for protecting, according to claim 1, wherein said teeth and said complementary teeth are curved or slanted so as to form a graduated abutment.

3. The device for protecting, according to claim 1, wherein said toothed sleeve is attached to said tube of said syringe.

4. The device for protecting, according to claim 1, wherein said first position corresponds to said toothed sleeve engaged to said sleeve cam at said teeth and complementary teeth, said first compression spring being extended between said abutment member of said sleeve cam and said complementary abutment member of said collar member and said second compression spring extended between said toothed sleeve and said sheath means, and
    wherein said second position corresponding to said toothed sleeve engaged to said protrusions of said interior volume of said collar member, said first compression spring extended between said abutment member of said sleeve cam and said complementary abutment member of said collar member and said second compression spring compressed between said toothed sleeve and said sheath means.

5. The device for protecting, according to claim 1, wherein said button means engages said sleeve cam to compress said first compression spring by said abutment member towards said complementary abutment member of said collar member, said sleeve cam pushing said toothed sleeve toward said screw threads, said sleeve cam stopping with said teeth of said toothed sleeve engage engaging said protrusions of said collar member and releasing said complementary teeth, and said first compression spring returning to full extension.

6. The device for protecting, according to claim 1, wherein said button means engages said sleeve cam to compress said first compression spring by said abutment member towards said complementary abutment member of said collar member, said complementary teeth of said sleeve cam engaging said teeth of said toothed sleeve until said teeth disengage said protrusions, and said first compression spring returns to full extension and said second compression spring returns to full extension.

7. The device for protecting, according to claim 1, wherein said toothed sleeve is placed on said syringe for a third position, said teeth of said toothed sleeve being shaped to actuate between the first, second and third positions, and said third position corresponding to said needle in a retracted position.

8. The device for protecting, according to claim 1, wherein said actuation means corresponds in shape to said syringe for fixed engagement of said toothed sleeve.

\* \* \* \* \*